US00PP08365P

United States Patent [19]

Vletter

[11] Patent Number: Plant 8,365

[45] Date of Patent: Sep. 7, 1993

[54] LILY PLANT NAMED MADRAS

[75] Inventor: Floris Vletter, Rijnsburg, Netherlands

[73] Assignee: Gebr. Vletter & J. A. Den Haan, Rijnsburg, Netherlands

[21] Appl. No.: 796,696

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new and distinct cultivar of lily plant named Madras, characterized by its upright flowers, intense bright yellow flower color, long stems, vigorous habit, numerous relatively short and narrow leaves, and by its floriferousness.

1 Drawing Sheet

The present invention comprises a new and distinct cultivar of lily, botanically known as Lilium, commercially known as Lilium asiatic hybrid, and hereinafter referred to by the cultivar name Madras. The parents were asiatic varieties belonging to division I described in "Classification of Lily Cultivars into Divisions" published by Victoria Mathews, The Royal Botanic Gardens, Kew (1989).

The new cultivar is a product of a planned breeding program which had the primary objective of creating new lily cultivars with a strong or intense yellow flower color, while also achieving other desired attributes in lily cultivars for cut flower production.

The new cultivar was originated from a hybridization made by the inventor in a controlled breeding program in Rijnsburg, The Netherlands in 1984. Both the male and female parents are unnamed seedlings.

The new cultivar was discovered and selected as one flowering plant within the progeny of the stated cross by the inventor in June 1984 in a controlled environment in Rijnsburg, The Netherlands.

The first act of asexual reproduction of the new cultivar was accomplished by the inventor when scales were taken from the initial selection in 1987 in a controlled environment in Rijnsburg, The Netherlands.

Horticultural examination of selected units has demonstrated that the combination of characteristics as herein disclosed for Madras are firmly fixed and are retained through successive generations of asexual reproduction.

The new cultivar has not been observed under all possible environmental conditions. The phenotype may vary significantly with variations in environment such as temperature, light intensity, and day length, without, however, any variation in genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of the new cultivar which in combination distinguish this lily as a new and distinct cultivar.

1. Brilliant solid yellow flower color;
2. Contrasting light brown to orange brown pollen color;
3. Vigorous growth habit;
4. Long stems;

5. Floriferous habit;
6. Numerous relatively short and narrow leaves;
7. Flowers are held upright.

Of the many commercial cultivars known to the present inventor, the most similar in comparison to the new cultivar is Latina. When flowering is forced under natural light, Madras produces an inflorescence approximately 36 days earlier than Stargazer, grown under the same conditions. Madras is fertile. In comparison to Latina, Madras has a lighter yellow flower color, more narrow leaves and lighter colored anthers.

The accompanying photographic drawing shows typical flower characteristics of the new cultivar, with colors being as true as possible with illustrations of this type. The photograph comprises a top perspective view showing several open flowers and buds at various stages.

In the following description, color references are made to The Royal Horticultural Society (RHS) Colour Chart. The color values were determined at Wageningen in 1988–1989 and at Rijnsburg in July 1991.

Origin: Seedling from Breeding Program.

Parentage:

*Seed parent.*—Unnamed seedling.

*Pollen parent.*—Unnamed seedling.

Classification:

*Botanical.*—Lilium.

*Commercial.*—Asiatic hybrid.

THE PLANT

Form: A single stem carrying numerous pedicels alternately arranged.

Height: Tall; height approximately 120 cm at time of opening of anthers of first flower, depending on growing conditions.

Growth habit: Vigorous.

Stem: Color 144B; angular in transverse section; internodal length uniform (1.5 cm); anthocyanin pigmentation present.

Foliage:

*Quantity.*—Numerous; approximately 130–150 leaves depending on growing conditions.

*Size of leaf.*—Mature leaves are short to medium in length (16 cm), and narrow in width (2 cm).

*Shape of leaves.*—Elliptical.

*Texture.*—Smooth with strong glossiness on upper side; no pubescence.

*Color.*—Medium green 137A.

Bulbs:

*Size.*—Outlet 6–22 cm.

*Color.*—White.

Roots: Both stem and contractile present.

THE BUD

Form: Tapering (like a lancet).

Size: 8 cm prior to opening.

Opening: Unfolds normally.

Color: 154B (prior to opening).

Tepals: Folded, three visible.

THE FLOWER

Blooming habit: Raceme.

Size: 16 cm in total diameter, depending on growing conditions.

Borne: Upright.

Shape: Generally in form of hexagonal star.

Tepalage:

*Number of tepals.*—Six.

*Arrangement.*—Three inner and three outer base portions of each tepal relatively narrow and with reduced overlap, slight marginal undulation outer tepals.

*Color.*—Upper surface: Intense bright yellow, slightly darker and more intense than 14A. Lower surface: Yellow 14A.

*Spotting or marking.*—None or very few tiny spots.

Nectaries and papillae: Present.

Pedicel:

*Length.*—8 cm (of first flower).

*Color.*—Medium green.

*Form.*—Slightly curved.

Texture: Ribbed and papillose.

Disease resistance: No disease problems noted to date.

Fragrance: Absent.

Lasting quality: Excellent.

REPRODUCTIVE ORGANS

Stamens, anthers:

*Arrangement.*—Anthers form a generally circular pattern.

*Length.*—Very short to short (5.5 cm).

*Number.*—Six.

*Filaments.*—Light yellow to yellow.

Pollen color: Light brown to orange brown.

Anther color: Yellow.

Pistils: One yellow style; total length of pistil is 7 cm.

Stigma: Red purple stigma.

Ovaries: Triangular in shape; other characteristics typical of asiatic lily varieties.

I claim:

1. A new and distinct cultivar of lily plant named Madras, as illustrated and described.

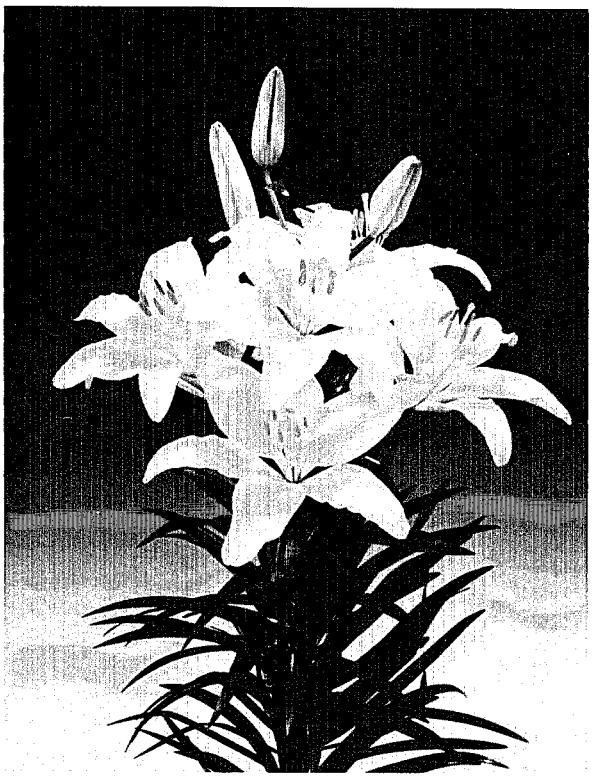

* * * * *